United States Patent [19]

Yanagibashi et al.

[11] Patent Number: 4,900,554
[45] Date of Patent: Feb. 13, 1990

[54] ADHESIVE DEVICE FOR APPLICATION TO BODY TISSUE

[75] Inventors: Norio Yanagibashi, Tokyo; Setsuo Iwasaki, Saitama; Takafumi Mizobuchi, Kagawa; Ryoji Konishi, Kagawa; Tatsuya Konishi, Kagawa; Takahiko Wato, Kagawa, all of Japan

[73] Assignee: Teikoku Seiyaku Co., Ltd., Kagawa, Japan

[21] Appl. No.: 137,034

[22] Filed: Dec. 23, 1987

[30] Foreign Application Priority Data

Dec. 24, 1986 [JP] Japan .................................. 61-310993

[51] Int. Cl.$^4$ .............................................. A61F 13/02
[52] U.S. Cl. .................................... 424/448; 424/449; 424/447
[58] Field of Search ........................ 424/448, 449, 435; 524/35

[56] References Cited

U.S. PATENT DOCUMENTS 4,668,232 5/1987 Cordes et al. .................... 424/448
4,738,848 4/1988 Yoshida et al. ................... 424/448

Primary Examiner—Ellis P. Robinson
Assistant Examiner—Leon R. Horne
Attorney, Agent, or Firm—Burns, Doane, Swecker & Mathis

[57] ABSTRACT

An adhesive device for application to body tissue having an adhesive layer and a backing layer positioned over one side of the adhesive layer. The adhesive layer includes one or more acrylic acid polymers having adhesive properties upon dissolution or swelling in water, and at least one water insoluble cellulose derivative. The backing layer is water insoluble or sparingly water soluble.

12 Claims, 1 Drawing Sheet

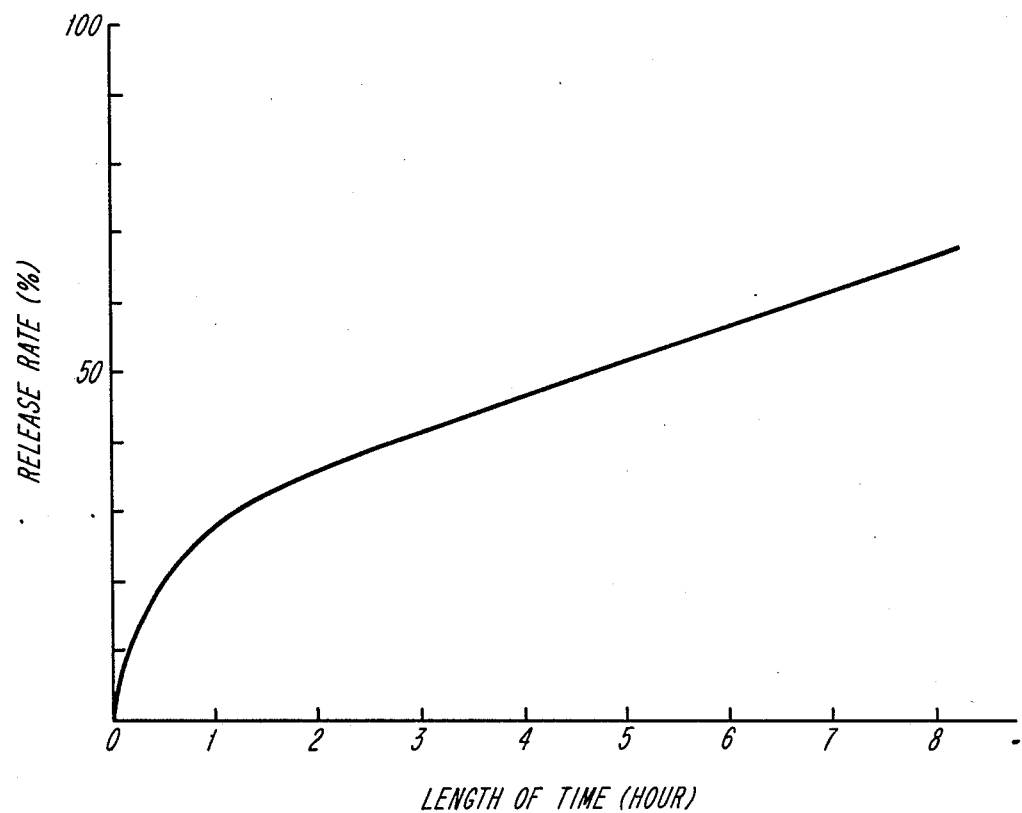

ADHESIVE DEVICE FOR APPLICATION TO BODY TISSUE

BACKGROUND OF THE INVENTION

1. Field of the Invention:

The present invention relates to novel adhesive devices for application to body tissue, to various processes for the preparation thereof, and to the use of such novel adhesive devices for sustained drug release and for protection of body tissue. In a preferred embodiment, the adhesive device is applied to the oral cavity. When applied to the oral cavity, the oral adhesive device sticks to oral mucosa or the tooth easily due to adhesiveness upon swelling or dissolution of the adhesive layer.

When used to protect wounds, diseased areas or other "ailing sites," therapy is efficient because of protection of the ailing sites and sustained drug release to the mucosal membrane, tooth or saliva.

2. Description of the Prior Art:

It has been known in this art to use various adhesive devices for the sustained release of drugs. Water soluble polymers dispersed in Plastibase are described in Japanese Takkaisho 51-38412 and Takaisho 53-86011. A tablet or sheet of polymer which becomes adhesive when contacted with saliva is disclosed by the following Japanese Tokkaisho: 54-41320, 54-41321, 55-62012, 55-92334, 55-83715, 55-84166, 55-84167, 55-83709, 55-83710, 56-18912, 56-68608, 58-213709, 59-48409, 59-181218, 59-186913, 59-232552, 59-232553, 60-116630, 60-116631, 60-215622.

A sheet made from a mixture of acrylic acid polymer and another polymer is disclosed by Takkaisho 61-249473.

The above devices, however, have the problems of relatively short residence time, insufficient protection of the ailing sites because of the lack of physical strength of the device itself, and foreign body sensation upon use, that is, a feeling of protrusion.

Further, a sheet made from a mixture of acrylic acid polymer (e.g. carboxyl- vinyl polymer) and polyvinyl acetate does not have enough adhesiveness and further shows a decrease in adhesiveness at 6 months after preparation.

SUMMARY OF THE INVENTION

It is accordingly an object of the invention to provide an adhesive device for application to body tissue such as the oral cavity.

It is another object of the invention to provide an adhesive device, as above, which easily adheres to the ailing site.

It is yet another object of the invention to provide an adhesive device, as above, having a good residence time.

It is still another object of the invention to provide an adhesive device, as above, which does not peel off during normal activity such as drinking or conversation.

It is yet another object of the invention to provide an adhesive device, as above, which does not give a foreign body sensation.

It is still another object of the invention to provide an adhesive device, as above, which is easy to use, and which provides the sustained release of a pharmaceutical preparation into the body tissue or saliva.

These objects are achieved by an adhesive device for application to body tissue, comprising an adhesive layer having an adhesive surface adherable to body tissue, and a water insoluble or sparingly water soluble backing layer secured over a surface of the adhesive layer opposite the adhesive surface and wherein the adhesive layer comprises a mixture of at least one acrylic acid polymer and a water insoluble cellulose derivative.

The objects of the invention are further achieved by a method for providing the sustained release of a drug to an individual comprising the steps of (a) applying to a body tissue of the individual an adhesive device comprising (1) an adhesive layer having an adhesive surface adherable to the body tissue and (2) a water insoluble or sparingly water soluble layer secured over a surface of the adhesive layer opposite the adhesive surface and wherein the adhesive layer comprises a mixture of at least one acrylic acid polymer, a water soluble cellulose derivative, and a pharmaceutical preparation; and (b) contacting the adhesive device with a bodily fluid, thereby releasing the pharmaceutical preparation into at least one of the body tissue and the bodily fluid.

BRIEF DESCRIPTION OF THE DRAWING

The single FIGURE illustrates the release rate of dibucaine hydrochloride in an adhesive device of the present invention.

DETAILED DESCRIPTION OF THE PREFERRED EMBODIMENTS

In the present invention, a sheet-like adhesive layer which includes an acrylic acid polymer exhibiting adhesiveness upon dissolution or swelling, and a water insoluble cellulose derivative, is secured to a backing layer which is water insoluble or sparingly water soluble.

The present invention thus provides for an adhesive device useful for example, in the oral cavity, which includes an adhesive layer comprising a mixture of an acrylic acid polymer and a water insoluble cellulose derivative, and a water insoluble or sparingly soluble backing layer.

The first characteristic of the present invention is that the device easily adheres to the ailing site in the oral cavity and that the adherence is sustained. Moreover, the adherence is not affected by any kind of oral movement such as drinking, eating, smoking or conversation. The second characteristic of the invention is that the adhesive device protects the ailing site because of its physical strength. The third characteristic is that the adhesive device gives less foreign body sensation because it becomes flexible upon swelling with saliva in the oral cavity, and also because it does not adhere to adjacent areas due to the water insoluble or sparingly soluble backing layer.

The fourth characteristic of the invention is that the release of the drug into tissue or saliva is sustained after application to oral mucosa when the drug is formulated in an adhesive layer.

The above characteristics of the present invention arise from the use of an adhesive layer which includes an acrylic acid polymer, showing adhesiveness by dissolution or swelling in water, and a water insoluble cellulose derivative whereby the adhesive layer is attached to a water insoluble or sparingly soluble backing layer on one side thereof. It is impossible to achieve the purpose of the present invention without all three components, that is, acrylic acid polymer, water insoluble cellulose derivative and a water insoluble or sparingly soluble backing layer.

Any kind of acrylic acid polymer can be used in the adhesive layer as long as the polymer or polymers show adhesiveness upon dissolution or swelling in water. For example, polyacrylic acid or partially cross-linked polyacrylic acid (acid type such as Carbopol) are preferable. The viscosity of the polyacrylic acid is preferably 100–200,000 cp (10% w/w aq. soln. 25° C.), most preferably 500–100,100 cp. Partially cross-linked polyacrylic acid is preferably Carbopol 934, 940, and 941 (BF Goodrich), Hiviswako 103, 104, 105 and 106 (Wako Junyaku).

As a water insoluble cellulose derivative, ethyl cellulose, carboxymethyl cellulose, calcium carboxymethyl cellulose, carboxymethylethyl cellulose, cellulose acetate, cellulose acetatephthalate, and hydroxypropyl methylcellulose phthalate can be used. However, one kind or combination of more than two kinds of the following polymers are preferable in terms of film forming capability and flexibility of the film: ethylcellulose, carboxymethylethyl cellulose, cellulose acetate, cellulose acetatephthalate and hydroxypropyl-methylcellulose phthalate. Although there is no limitation to the description of ethylcellulose, it is preferable that its ethoxy content is 45–49.5% and that its viscosity is 3–350 cp, especially 10–100 cp (5% w/w in toluene:ethanol=80:20, 25° C.). For carboxymethylethyl cellulose, it is preferable that its carboxymethyl content is 4.8–27.2% and that the ethoxy content is 17.4–46.2%. The acetyl content of cellulose acetate is preferably 29.0–44.8%. For cellulose acetate-phthalate, it is preferable that its acetyl content is 17–22.0% or its phthalate content is 30.0–40.0%. Hydroxypropylmethylcellulose phthalate is preferably hydroxy-propylmethylcellulose phthalate 200731 or 200824 (Japanese Pharmacopeia).

The ratio (w/w) of acrylic acid polymer to water insoluble cellulose derivative is preferably 99:1–50:50, most preferably 98:2–70:30. This ratio gives good and sustained adhesiveness of an adhesive layer and does not give any foreign body sensation.

Any material can be used as a backing layer as long as it supports the adhesive layer, for example, polymer film, paper cloth, non-woven cloth or aluminum sheet. Considering the factor of edibility, however, a film consisting of one or two kinds of the following polymers is preferable: ethylcellulose, cellulose acetate, cellulose acetatephthalate, hydroxypropyl methylcellulose phthalate, vinylacetate resin or a pharmacologically acceptable water soluble polymer which is insolubilized by cross linking.

Although there is no limitation to the thickness of the adhesive layer and the backing layer, the thickness of the adhesive layer is preferably 10–1000 micrometers, especially 20–200 micrometers and the thickness of the backing layer is preferably 1–100 micrometers, especially 5–30 micrometers. The device shape can be modified to any shape depending on the ailing site.

The adhesive device of the present invention can incorporate any compound into the components described above. For example, glycerin or polyethylene glycol can be incorporated as a plasticizer to make the adhesive layer flexible; polyalcohols such as propylene glycol can be used to control drug release; absorption promoters such as surfactants and Azone can be added; scents, flavoring agents, coloring agents, and preservatives can be also incorporated. Where one or more of these additional compounds are present, the total content of acrylic acid polymer and water insoluble cellulose derivative in the adhesive layer is preferably more than 50%.

Drugs (i.e., pharmaceutical preparations) can be incorporated into the adhesive device, and the duration of drug action is prolonged because of sustained release of the drug from the adhesive device. Although any drug can be used depending on the purpose of therapy, the following are exemplary:

1. anti-inflammatory, analgesic agents: content 0.1–5%
2. steroidal anti-inflammatory agents: content 0.002–0.5%
3. antihistamines: 0.1–2%
4. local anesthetics: 0.05–2%
5. bactericides and disinfectants: 0.01–10%
6. vasoconstrictor: 0.01–1%
7. hemostatics: 0.05–1%
8. chemotherapeutic drugs: 0.05–1%
9. antibiotics: 0.001–10%

Examples of anti-inflammatory, analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc.

Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone dipropionate, etc.

Examples of antihistamines include diphenhydramine hydrochloride, diphenhydramine salicylate, diphenhydramine, chlorpheniramine hydrochloride, chlorpheniramine maleate, isothipendyl hydrochloride, tripelennamine hydrochloride, promethazine hydrochloride, methdilazine hydrochloride, etc.

Examples of local anesthetics include dibucaine hydrochloride, dibucaine, lidocaine hydrochloride, lidocaine, benzocaine, p-buthylaminobenzoic acid 2-(diethylamino)ethyl ester hydrochloride, procaine hydrochloride, tetracaine hydrochloride, chloroprocaine hydrochloride, oxyprocaine hydrochloride, mepivacaine, cocaine hydrochloride, piperocaine hydrochloride, etc.

Examples of bacterioides and disinfectants include thimerosal, phenol, thymol, benzalkonium chloride, benzethonium chloride, chlorhexidine, povidone iode, cetylpyridinium chloride, eugenol, trimethylammonium bromide, etc.

Examples of vasoconstrictors include naphazoline nitrate, tetrahydrozoline hydrochloride, oxymetazoline hydrochloride, phenylephrine hydrochloride, tramazoline hydrochloride, etc.

Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, etc.

Examples of antibiotics include penicillin, meticillin, oxacillin, cefalotin, cefaloridin, erythromycin, lincomycin, tetracycline, chlortetracycline, oxytetracycline, metacycline, chloramphenicol, kanamycin, streptomycin, gentamicin, bacitracin, cycloserine, etc.

The content of the pharmaceutical can be varied depending on the particular one employed. In general, however, the pharmaceutical content is 0.001–20%, and preferably 0.002–10% of the adhesive layer.

The method of preparation for the present device is not limited and various methods can be used, for example the adhesive layer components can be dissolved in solvent, spread on a flat surface and dried to form an adhesive layer. The backing layer components in solvent solution can then be spread over the adhesive layer and dried to form a backing layer.

The adhesive device can be used without incorporating a drug, for example, as a surgical pack or it can be used for therapeutic use with a drug in the adhesive layer. To apply to the oral mucosal membrane, the adhesive layer is placed on the ailing site. The adhesive layer becomes sticky by dissolution or swelling with saliva, whereupon it sticks to the ailing site.

When applied to an oral cavity, the present oral adhesive device easily sticks to the ailing site, its adhesiveness is sustained, it protects the ailing site, it gives less foreign body sensation, and its drug release is stable and sustained. The device thus provides protection of the ailing site and sustained drug action.

The following examples illustrate the invention. Percentages in the various formulations refer to weight percentage.

EXAMPLE 1

Test of adhesiveness to lower jaw lip side gum, protectability and protrusion-like feeling in human volunteers.

Adhesive devices of the present invention (A,B,C,D, and E, the composition of each adhesive layer being shown in Table 1) and devices outside the scope of the invention were applied to the lower jaw lip side gums of healthy male volunteers. Activities of the volunteers were restricted according to the schedule below and the adhesiveness measured by the length of time before the device peeled off. Protectability was determined by the area of a patch five hours after application: no area change compared to the initial area—very good; more than ⅔ of the initial area remaining—good; more than ½ of the initial area remaining—adequate; less than ½ remaining—unsatisfactory. The degree of foreign body sensation was determined by the questionnaire after the test:very strong foreign body sensation (+++); strong foreign body sensation (++); foreign body sensation (+); slight foreign body sensation (±); no foreign body sensation (−). The results are summarized in Tables 2–4, which show the results both for each volunteer and the average.

TABLE 1

| Formulas of the Present Invention | | | | | |
|---|---|---|---|---|---|
| 1. Adhesive Layer | A | B | C | D | E |
| Acrylic acid polymer[1] polyacrylic acid | 18 | 16 | 14 | 12 | 10 |
| water insoluble cellulose derivative[2] ethylcellulose | 2 | 4 | 6 | 8 | 10 |
| glycerin-fatty acid ester[3] | 2 | 2 | 2 | 2 | 2 |

[1]Polyacrylic acid used had a viscosity of 100,000 cps for 10% aq. soln.
[2]Ethylcellulose used was Ethocel 45 cps (Dow Chemical, standard type, ethoxy content 48–40.5%, viscosity of 5% soln. in toluene:ethanol = 80:20 is 41–49 cps).
[3]Glycerin-fatty acid ester used was Nikkol Mas-ASE (glycerin monosterate, Nikko Chemicals). The same glycerin-fatty acid ester was used for the other examples and the comparison samples.

Adhesive layer components were dissolved in ethanol, mixed, spread on a waxed paper, and dried at 40° C. The backing layer components were dissolved in ethanol and spread over the dried adhesive layer and dried at 40° C.

| Comparison Sample F | |
|---|---|
| 1. Adhesive Layer | |
| Polyacrylic Acid (100,000 cps at 10%) | 18 |
| Ethylcellulose (Ethocel 45 cp) | 2 |
| Glycerine-fatty acid Ester | 2 |

The preparation method was the same as that for the device of the present invention except that no backing layer was used.

| Comparison Sample G | |
|---|---|
| 1. Adhesive Layer | |
| Ethylcellulose (Ethocel 45 cp) | 20 |
| Glycerine-fatty acid Ester | 2 |
| 2. Backing Layer | |
| Ethylcellulose (Ethocel 100 cp) | 14 |
| Castor Oil (plasticizer) | 6 |

The preparation method was the same as that for the invented device.

| Comparison Sample H | |
|---|---|
| 1. Adhesive Layer | |
| Polyacrylic Acid (100,000 cps at 10%) | 20 |
| Glycerin-fatty acid Ester | 2 |
| 2. Backing Layer | |
| Ethylcellulose (Ethocel 45 cp) | 14 |
| Castor Oil (plasticizer) | 6 |

The preparation method was the same as that for the invented device.

| Comparison Sample J | |
|---|---|
| 1. Adhesive Layer | |
| Polyacrylic Acid (100,000 cps at 10%) | 10 |
| Hydroxypropyl Cellulose (Nihon Soda, HPC-L) | 10 |
| Glycerin-fatty acid Ester | 2 |
| 2. Backing Layer | |
| Ethylcellulose (Ethocel 100 cp) | 14 |
| Castor Oil (plasticizer) | 6 |

The preparation method was the same as that for the invented device.

| Comparison Sample K | |
|---|---|
| 1. Adhesive Layer | |
| Hydroxypropyl Cellulose (Nihon Soda, HPC-L) | 20 |
| Polyacrylic Acid (Carbopol 934) | 20 |

The components were mixed and compressed to obtain tablets of Comparison Example K.

| Schedule | |
|---|---|
| Time | Activity |
| 8:00 | application of device |
| 10:00 | tea |

| Schedule | |
|---|---|
| Time | Activity |
| 12:00 | lunch |
| 13:00 | determination of protectability |
| 15:00 | tea |
| 18:00 | final observation |

From the results in Tables 2–4, it can be seen that the device of the invention has a longer adhesion time and better protectability than the comparison devices. Moreover, devices A–E had less foreign body sensation.

EXAMPLE 2

In Vitro Drug Release

Dibucain Hydrochloride was incorporated (1.0% w/w) into device A in Example 1 and the in vitro release was measured.

A millipore filter was placed in a beaker filled with 100 ml of water. A device of the invention having a 20 mm diameter was placed on a millipore filter and the dibucaine concentration in water was measured at regular time intervals.

The result is shown in the Figure. It is obvious from the Figure that the release rate is constant between 1 and 8 hours and it is considered that drug action after application of the present device to the oral cavity can be sustained.

Although example formulas are shown below, the present invention is not to be limited thereby. Percentages in the examples are by weight.

Example Formula 1

| 1. Adhesive Layer | |
|---|---|
| Polyacrylic Acid (100,000 cps at 10%) | 20.0% |
| Ethylcellulose (Ethocel 45 cp) | 3.0 |
| Glycerin-Fatty acid Ester | 1.0 |
| Methylparaoxybenzoic Acid | 0.01 |
| Ethanol | 75.99 |
| 2. Backing Layer | |
| Etycellulose (Ethocel 45 cp) | 10.0% |
| Castor Oil (plasticizer) | 5.0 |
| Ethanol | 85.0 |

Adhesive layer components were dissolved, mixed, spread on waxed paper and dried at 30° C. Then the backing layer components were dissolved, spread over the adhesive layer and dried at room temperature. This device is used as an oral bandage to protect and promote the healing of an ailing site in the oral cavity.

Example Formula 2

| 1. Adhesive Layer | |
|---|---|
| Polyacrylic Acid (30,000–50,000 at 8% aq. soln) | 25.0% |
| Cellulose Acetate (Daicel, Degree of Oxidation 55%) | 3.5 |
| Acetone | 71.5% |
| 2. Backing Layer | |
| Cellulose Acetate (Degree of Oxidation 55%) | 10.0% |
| Castor Oil | 5.0 |
| Acetone | 85.0 |

Adhesive layer components were dissolved, mixed, spread over a waxed paper and dried at 40° C. to obtain an adhesive layer. Backing layer components were dissolved and sprayed on one side of the adhesive layer to thereby obtain the present device. This device can be used as an oral bandage.

Example Formula 3

| 1. Adhesive Layer | |
|---|---|
| Polyacrylic Acid (Carbopol 941, Goodrich) | 10.0% |
| Ethylcellulose (Ethocel 100cp) | 2.0 |
| Glycerin-Fatty acid Ester | 1.0 |
| Propylparaoxybenzoic Acid | 0.02 |
| Propylene Glycol | 5.0 |
| Dibucaine Hydrochloride | 0.2 |
| Ethanol | 81.78 |
| 2. Backing Layer | |
| Etylcellulose (Ethocel 100 cp) | 10.0 |
| Castor Oil | 5.0 |
| Ethanol | 85.0 |

Adhesive layer components were dissolved, mixed, spread on a waxed paper and dried at 40° C. to obtain an adhesive layer. Backing layer components were dissolved, spread over the adhesive layer and dried at 40° C. The device is used as a preanesthetic for dental therapy.

Example Formula 4

| 1. Adhesive Layer | |
|---|---|
| Polyacrylic Acid (Wako Junyaku, Hiviswako 104) | 10.0% |
| Hydroxypropyl methylcellulose phthalate (Shinetsu Chemical, HPMCP200731) | 2.0 |
| Hydroxypropyl cellulose (Nisso HPC-L) | 5.0 |
| Polyethylene Glycol 400 | 5.0 |
| Tranexamic Acid | 1.0 |
| Etanol:Water (80:20) Mixture | 77.0 |
| 2. Backing Layer | |
| Ethylcellulose (Ethocel 10 cp) | 20.0 |
| Castor Oil | 10.0 |
| Ethanol | 70.0 |

Adhesive layer components were dissolved, mixed, spread on waxed paper and dried at 40° C. to obtain an adhesive layer. Backing layer components were dissolved, spread over the adhesive layer and dried at 40° C. This device can be used as a hemostatic for periodontitis and also after pulling out a tooth.

While the above description is primarily directed to use of the adhesive device of the invention in the oral cavity, it will be appreciated that the invention can be used in other applications such as intravaginal, etc.

TABLE 2

| | Length of Adhesive Time (hours) | | | | | |
|---|---|---|---|---|---|---|
| Volunteer No. | 1 | 2 | 3 | 4 | 5 | Ave. |
| Sample A | >10 | >10 | 8 | >10 | >10 | 9.6 |
| Sample B | 9.5 | >10 | >10 | >10 | 9 | 9.7 |
| Sample C | 8 | 9.5 | 7 | 8.5 | >10 | 8.6 |
| Sample D | 6.5 | 7 | 8 | 6 | >10 | 7.5 |
| Sample E | 5.5 | 6 | 8 | 7.5 | 6.5 | 6.7 |
| Comparison Sample F | 4 | 8.5 | 4 | 6 | 4 | 5.3 |
| Comparison Sample G | 0 | 0 | 0 | 0 | 0 | 0 |
| Comparison Sample H | 2 | 4 | 5.5 | 4 | 6 | 4.3 |
| Comparison Sample I | 4 | 6 | 4 | 5 | 7 | 5.2 |
| Comparison | 6 | 8 | 8 | 6 | 6 | 6.8 |

TABLE 2-continued

| Volunteer No. | Length of Adhesive Time (hours) | | | | | |
|---|---|---|---|---|---|---|
| | 1 | 2 | 3 | 4 | 5 | Ave. |
| Sample J | | | | | | |
| Comparison Sample K | 4 | 6 | 8 | 6 | 4 | 5.6 |

TABLE 3

| Volunteer No. | Protectibility | | | | | |
|---|---|---|---|---|---|---|
| | 1 | 2 | 3 | 4 | 5 | Ave. |
| Sample A | ◉ | ◉ | ◉ | ◉ | ◉ | ◉ |
| Sample B | ◉ | | ◉ | ◉ | ◉ | ◉ |
| Sample C | ◉ | ◉ | ○ | △ | ◉ | ○ |
| Sample D | ○ | ○ | ◉ | ◉ | ○ | ○ |
| Sample E | △ | ◉ | ○ | △ | ○ | ○ |
| Comparison Sample F | X | ◉ | X | ○ | X | △ |
| Comparison Sample G | X | X | X | X | X | X |
| Comparison Sample H | X | X | △ | X | ○ | △ |
| Comparison Sample I | X | ○ | X | △ | △ | △ |
| Comparison Sample J | X | ○ | ○ | △ | X | △ |
| Comparison Sample K | X | △ | ○ | ○ | X | △ |

Legend:
◉ Good
○ Very Good
△ Adequate
X Unsatisfactory

TABLE 4

| Volunteer No. | Degree of Foreign Body Sensation | | | | | |
|---|---|---|---|---|---|---|
| | 1 | 2 | 3 | 4 | 5 | Ave. |
| Sample A | − | − | ± | ± | − | − |
| Sample B | − | ± | − | ± | − | − |
| Sample C | − | − | − | ± | − | − |
| Sample D | − | ± | ± | ± | ± | ± |
| Sample E | − | − | ± | ± | ± | ± |
| Comparison Sample F | ++ | ++ | +++ | ++ | + | ++ |
| Comparison Sample G | − | − | − | − | − | − |
| Comparison Sample H | ± | ± | ± | − | ± | ± |
| Comparison Sample I | + | − | − | ± | + | ± |
| Comparison Sample J | + | + | ++ | + | − | + |
| Comparison Sample K | + | ++ | + | ++ | ++ | ++ |

Legend:
+++ Very strong foreign body sensation
++ Strong foreign body sensation
+ Foreign body sensation
± Slight foreign body sensation
− No foreign body sensation

What is claimed is:

1. An oral cavity adhesive device for application to a mucous membrane or oral cavity tissue of an individual, comprising:
    an adhesive layer including a mixture of at least one acrylic acid polymer, a water-insoluble cellulose derivative, and a pharmaceutical preparation, said adhesive layer having an adhesive surface adherable to a mucous membrane or oral cavity tissue; and
    a water-insoluble or sparingly water-soluble backing layer secured over said adhesive layer on a side opposite the adhesive surface;
    wherein said acrylic acid polymer exhibits adhesiveness upon dissolution or swelling when applied to the mucous membrane or oral cavity tissue, and wherein the weight ratio of acrylic acid polymer to water-insoluble cellulose derivative is within a range which provides sustained adhesiveness of the adhesive layer with substantially no foreign body sensation.

2. An adhesive device as claimed in claim 1, wherein the water-insoluble cellulose derivative is ethyl cellulose, carboxymethyl cellulose, calcium carboxymethyl cellulose, carboxymethylethyl cellulose, cellulose acetate, cellulose acetatephthalate or hydroxypropylmethyl cellulose phthalate.

3. An adhesive device as claimed in claim 1, wherein the weight ratio of acrylic acid polymer to water-insoluble cellulose derivative is from about 99:1 to about 50:50.

4. An adhesive device as claimed in claim 1, wherein the weight ratio of acrylic acid polymer to water-insoluble cellulose derivative is from about 98:2 to about 70:30.

5. An adhesive device as claimed in claim 1, wherein the backing layer is ethylcellulose, cellulose acetate, cellulose acetatephthalate, hydroxypropylmethyl cellulose phthalate, vinyl acetate resin or a pharmacologically acceptable water-soluble polymer insolubilized by cross-linking.

6. A method for providing the sustained release of a pharmaceutical preparation to an individual, comprising the steps of:
    (a) applying to a mucous membrane or oral cavity tissue of the individual an adhesive device comprising:
        (1) an adhesive layer including a mixture of at least one acrylic acid polymer which exhibit adhesiveness upon dissolution or swelling when applied to said mucous membrane or oral cavity tissue and a water-insoluble cellulose derivative, and further including a pharmaceutical preparation; and
        (2) a water-insoluble or sparingly water-soluble backing layer secured over said adhesive layer on a side opposite the adhesive surface; and
    (b) contacting said adhesive device with a bodily fluid, thereby releasing said pharmaceutical preparation from said adhesive layer in a controlled manner;
    wherein the weight ratio of acrylic acid polymer to water-insoluble cellulose derivative is within a range which provides sustained adhesiveness of the adhesive layer with substantially no foreign body sensation.

7. A method as claimed in claim 6, wherein the adhesive device is applied to oral cavity tissue.

8. A method as claimed in claim 6, wherein the oral cavity tissue comprises gingival tissue, lip tissue or a tooth.

9. An adhesive device as claimed in claim 1, wherein said pharmaceutical preparation comprises an analgesic inflammatory agent, a steroidal anti-inflammatory agent, an antihistimine, a local anesthetic, a bactericide, a disinfectant, a vasoconstriction, a hemostatic, a chemotherapeutic drug or an antibiotic, said pharmaceutical preparation being present in said adhesive layer in an amount of from about 0.001 to about 20 percent by weight.

10. An adhesive device as claimed in claim 1, wherein said pharmaceutical preparation comprises methyl-paraoxybenzoic acid.

11. An adhesive device as claimed in claim 1, wherein said pharmaceutical preparation comprises dibucaine hydrochloride.

12. An adhesive device as claimed in claim 1, wherein said pharmaceutical preparation comprises tranexamic acid.

* * * * *